United States Patent [19]

Faith, Jr.

[11] 4,348,886
[45] Sep. 14, 1982

[54] MONITOR FOR OXYGEN CONCENTRATION IN ALUMINUM-BASED FILMS

[75] Inventor: Thomas J. Faith, Jr., Lawrenceville, N.J.

[73] Assignee: RCA Corporation, New York, N.Y.

[21] Appl. No.: 208,704

[22] Filed: Nov. 19, 1980

[51] Int. Cl.³ ............................................. G01N 27/12
[52] U.S. Cl. ....................................... 73/19; 118/712; 427/8
[58] Field of Search ................... 73/19, 23; 118/664, 118/712, 713, 714; 427/8, 9, 10, 99; 29/574; 428/457

[56] References Cited

U.S. PATENT DOCUMENTS 4,121,537 10/1978 Maruyama et al. ................ 118/664
4,302,498 11/1981 Faith, Jr. .............................. 428/209

FOREIGN PATENT DOCUMENTS 454364 9/1936 United Kingdom ................ 118/713

OTHER PUBLICATIONS

E. M. Da Silva et al., "Fabrication of Aluminum Oxide Films," *IBM Technical Disclosure Bulletin*, vol. 4, No. 6, pp. 6-7, Dec. 1961.

A. Kubovy et al., "The Influence of Residual Gas Pressure on the Stress in Aluminum Films," *Thin Solid Films*, 42, pp. 169-173, 1977.

*Primary Examiner*—Stephen A. Kreitman
*Attorney, Agent, or Firm*—Birgit E. Morris; Donald S. Cohen; Joseph D. Lazar

[57] ABSTRACT

The ratio of oxygen concentration to aluminum concentration in an aluminum film deposited in a vacuum chamber on an integrated circuit (IC) substrate is monitored by measuring either the resistivity or the resistance of a film of aluminum being simultaneously deposited film on a monitor substrate. The monitor substrate is arranged within the vacuum chamber such that the film of aluminum thereon has a concentration ratio of oxygen to aluminum that is significantly higher than the concentration ratio of oxygen to aluminum flux in the IC substrate film. This is done by reducing the aluminum flux or increasing the oxygen flux on the monitor substrate film. A measurement of the resistivity (or resistance) of the monitor substrate aluminum film is indicative of the resistivity and thus the oxygen concentration of the IC film.

15 Claims, 12 Drawing Figures

MONITOR FOR OXYGEN CONCENTRATION IN ALUMINUM-BASED FILMS

BACKGROUND OF THE INVENTION

This invention relates to a monitor for determining the oxygen concentration in a reactive metal film deposition, particularly, the oxygen content in an aluminum film deposited in a vacuum chamber containing residual oxygen species such as water vapor and/or added oxygen.

The properties of aluminum integrated-circuit metallizations are profoundly affected by impurities which are incorporated in the aluminum during film deposition. Elements, such as copper and oxygen, have been deliberately incorporated in aluminum films to provide increased resistance to electromigration failure in circuits operating at high-current densities. Silicon has been added to aluminum to inhibit junction spiking during the contact alloying process, and it has recently been shown that periodic addition of oxygen to aluminum during film deposition eliminates the growth of hillocks which otherwise occurs during the alloying process. See my copening patent application, Ser. No. 201,438, filed on Oct. 28, 1980, now U.S. Pat. No. 4,302,498, entitled "LAMINATED CONDUCTING FILM ON AN INTEGRATED CIRCUIT SUBSTRATE AND METHOD OF FORMING THE LAMINATE" for a detailed description of this process.

Oxygen is ubiquitous in aluminum integrated-circuit films. In the absence of a deliberate oxygen input, the principal source of oxygen is residual $H_2O$ in the vacuum system at the start of film deposition. Residual gas pressure in the vacuum chamber during deposition is the $10^{-6}$ Torr range. Typically, over 90 percent of this is water vapor outgassing from the chamber walls. A fraction of the water vapor molecules which impinge on the substrate react with the growing aluminum film. Hydrogen is usually released in such reactions, but the oxygen is adsorbed and incorporated in the film. Typical oxygen concentrations in a film deposited with no deliberate oxygen inputs are on the order of 0.1 percent. However, wide variations in concentration can occur in climates where variations in relative humidity are experienced, and/or where throughput considerations cause vacuum-system pumpdown times and maintenance schedules to be kept at a minimum.

It is known that oxygen (1) increases aluminum film hardness and resistivity; (2) decreases as-deposited film stress; (3) increases resistance to electromigration; (4) decreases grain size; and (5) eliminates hillock growth, given the proper oxygen-input sequencing conditions. In spite of these important influences on film properties, there are no methods for monitoring oxygen concentrations in aluminum films which are useful in terms of being readily applied to factory situations. Residual gas analysis involves expensive, sophisticated equipment, and the relationship between the data obtained and oxygen concentration in the film is tenuous. Materials analysis techniques such as Secondary Ion Mass Spectrometry (SIMS) also involve expensive equipment and cannot provide results immediately after the completion of film deposition.

A simple method and apparatus for determining oxygen concentration would therefore provide a valuable process-control monitor for films deposited in the residual vacuum-chamber environment, and also provide an important tool in the development of films with deliberate oxygen additions.

SUMMARY OF THE INVENTION

The present invention uses film resistivity as the monitored parameter for both film types. Aluminum is deposited as a film simultaneously on an integrated circuit substrate and a monitor substrate. The film deposited on the monitor substrate is arranged to have a ratio of oxygen to to aluminum concentration that is greater than the oxygen concentration to aluminum concentration ratio of the IC substrate film. A measurement of the sheet resistance of the monitor substrate film is indicative of the resistivity and thus the oxygen concentration of the IC film.

The resistivity measurement is fast and easy to interpret, and bears a direct relationship to the oxygen concentration in the film. Its major disadvantage is the relative insensitivity of film resistivity to oxygen concentration for concentrations of oxygen below approximately 5 percent. Accordingly, the present invention is directed to the enhancement of the sensitivity of resistance-monitor films relative to that of films deposited in the same deposition run on the integrated-circuit substrates. Each of these approaches involves positioning the monitor substrate so that the substrate experiences a higher oxygen specie-to-aluminum flux ratio (and conseqently a higher oxygen concentration) than the integrated-circuit substrate.

DETAILED DESCRIPTION OF THE PREFERRED EMBODIMENT

The invention is typically practiced in the metallization of integrated circuit wafers. Any of the known vacuum deposition systems may be used under certain conditions as will be described. There are three general kinds of vacuum deposition systems in which integrated-circuit metallizations are customarily deposited. First, there is a magnetron sputtering system operated in a vacuum which is back-filled with argon to a pressure of typically $2.5 \times 10^{-3}$ Torr. The second type of deposition system is an electron beam (E-beam) evaporator operating at high vacuum, for example, at $5 \times 10^{-6}$ Torr. The third class of deposition systems comprises evaporators in which the aluminum is evaporated from heated filaments or from rf heated crucibles.

Figure 1:
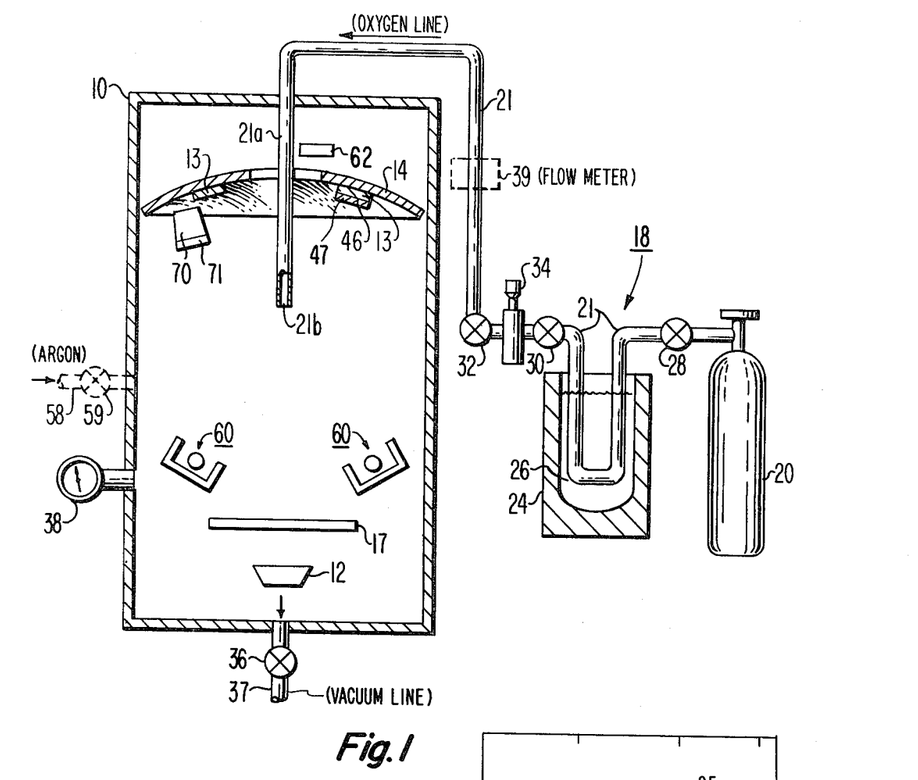
FIG. 1 is a schematic of one form of vacuum deposition apparatus useful in practicing the invention.

The apparatus illustrated in FIG. 1 represents any of the above enumerated deposition systems. A vacuum deposition chamber 10 is provided with a conventional source 12 of aluminum suitably positioned within the chamber. Suitable sources of aluminum include any of the known boats, strips, crucibles, helical coils, or sputtering targets suitably energized to provide an aluminum atom flux to substrates 13. Substrates 13 are thermally oxidized silicon wafers with contact openings or cuts formed therein for access to the surface of the silicon material to which conductive contact is to be made. These substrates are disposed on a substrate holding fixture 14 preferably of the known planetary type adapted to be both rotated and revolved over the aluminum source 12. A suitable source of power, not shown, is provided to the apparatus as required to generate the flux or stream of aluminum atoms from the source 12.

A moveable shutter 17 is provided to interrupt the path of atoms from the source 12 to prevent deposition of the atoms of aluminum on the substrate 13 during warm-up cycles or any other steps of the process during which it is desired that no deposition on the substrate occurs.

An oxygen source apparatus 18 is provided, when desired, to periodically introduce oxygen into the chamber during the process of depositing the aluminum on the substrates. Apparatus 18 includes a tank 20 containing oxygen which is conducted into the chamber 10 by an oxygen supply line 21 typically ¼" OD copper tubing connected to line 21a within the chamber 10 providing oxygen to the chamber through aperture 21b. Line 21 is passed through a cold trap 24 containing a suitable coolant 26, such as a dry ice and alcohol mixture. Oxygen flow is regulated by regulator 28 and needle valve 34. Shut off valves 30 and 32 in line 21 are provided to stop and start the flow of oxygen into the chamber 10. Valves 30 and 32 are preferably closely positioned adjacent to the needle valve 34 to regulate the flow of oxygen to the chamber in such a way as to prevent sudden bursts of oxygen after the pressure reduction is achieved by the needle valve 34. A vacuum line 37 coupled to vacuum pumps, not shown, provide means to exhaust the interior of chamber 10 by control valve 36. A Bayard-Alpert ion gauge 38 is provided to indicate (1) the pressure within the chamber and also (2) the oxygen fill pressure which is directly proportional to the oxygen flow rate from oxygen source 18 into the chamber 10. In the alternative, a flow meter 39 may be provided in the inlet line such as line 21 from the oxygen source into the chamber to measure directly the flow of oxygen into the chamber 10. Nevertheless, means is still needed to indicate the pressure within the chamber for vacuum control purposes and the like. Accordingly, the Bayard-Alpert ion gauge 38 is used for that purpose although any other convenient means to measure pressure may be used for this purpose. The manner of determining the pressure in a chamber and determining the flow rate of oxygen into a chamber are well known procedures in the art.

For apparatus which is to provide aluminum to the substrate by the sputtering technique, argon is required during the process. Accordingly, an inlet source 59 of argon is provided with a cut-off regulating valve 59.

Figure 2:
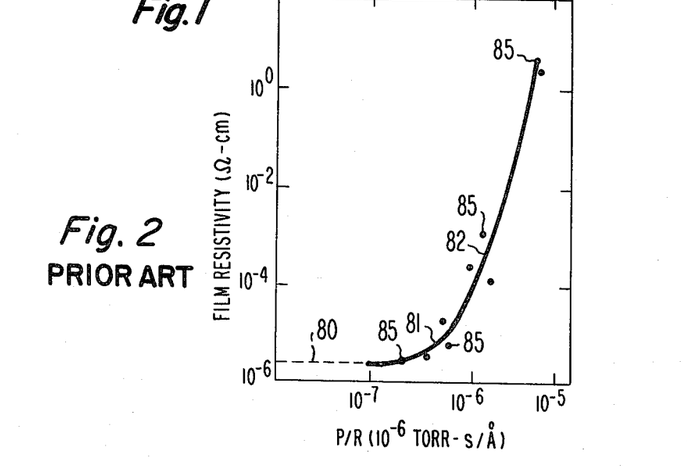
FIG. 2 is a plot of the resistivity of a film of aluminum versus the ratio of oxygen pressure to aluminum deposition rate.

According to the invention, a monitor substrate, represented in FIG. 1 by reference numeral 70, is positioned near the substrate 13. Substrate 70 has at least one major surface onto which a film 71 of aluminum is deposited. Such a film 71 of aluminum is deposited on the substrate 70, concurrently with the film 47 of aluminum deposited on the surface 46 of IC substrates 13 and is arranged to be provided with a ratio of oxygen to aluminum that is greater than the ratio of oxygen to aluminum in the film 47. The resistivity of the monitor film 71 has a determinable relation to the concentration of oxygen in the IC substrate 13 film 47. The resistivity of the film 71 is a parameter calculated from the sheet resistance of the film suitably measured by a four-point probe technique and the thickness of the film suitably measured by a thickness monitor such as a quartz-crystal film thickness monitor 62 or a Tencor profilometer, both well known in the art. The equation for calculating resistivity $\rho$ in $\Omega$-cm is $$\rho = r \times t \tag{1}$$

where r is the resistance in ohms per square and t is the film thickness in centimeters. The principle by which a determination of the relationship of oxygen concentration to resistivity can be understood by reference to FIG. 2.

FIG. 2, in which aluminum film resistivity is plotted versus oxygen pressure during film deposition, demonstrates how the sensitivity of a resistance monitor increases with increasing ratio of oxygen flux to aluminum flux on the growing film. The ordinate represents the film resistivity $\rho$ in $\Omega$-cm. The abscissa represents the ratio P/R where P is the gas pressure in Torr and R is the deposition rate in angstroms per second. The gas can be residual water vapor or a mixture of water vapor and added oxygen. The flux of such oxygen-containing species on the film 71 growing on monitor substrate 70 and on the film 47 growing on IC substrate 13 is proportional to the pressure, P.

At low pressures (approximately $10^{-7}$–$10^{-6}$ Torr), the slope of curve portion 80 is very low (substantially flat) indicative of resistivity being insensitive to changes in pressure. Since actual measurements were not made, curve portion 81 is drawn as a dotted line. Curve 80 is the oxygen-pressure regime in which all integrated-circuit metallizations are typically deposited. This dotted line represents the resistivity of pure bulk aluminum and, consequently, represents the asympotic resistivity for highly-pure aluminum thin films. However, as oxygen pressure continues to increase, the slope of the curve also increases, starting at knee portion 81, at first gradually and then more and more precipitiously as along portion 82. While the breakoff pressure of such curves varies widely with aluminum deposition rate and with the system in which the deposition is run, curves with the same shape as FIG. 2 have been reported by several investigators. See, for example, A. Kubovy and M. Janda, Thin Solid Films 42, 169 (1977). A monitor (such as monitor 70) operating in the high slope region viz., region 82, of this curve will be very sensitive to small changes in pressure, or equivalently, to small changes in oxygen-to-aluminum flux ratio. In a deposition in which oxygen is deliberately added (as by apparatus 18 of FIG. 1), a monitor substrate (70) will experience a high oxygen-to-aluminum flux if it is placed in a region of high oxygen flux, i.e., very close to a concentrated oxygen source, and/or if it is placed in a region of low aluminum flux. In a deposition in the residual chamber environment (unless there is a local region suspected of heavy water-vapor outgassing), the way to achieve a high oxygen-to-aluminum flux ratio is to place the monitor in a region in which it experiences a much lower aluminum flux than the integrated-circuit substrates. This arrangement is used in the embodiment shown in FIG. 3 to be described.

Aluminum flux reduction is accomplished in a straightforward manner in E-beam deposition systems. E-beam system pressure during all alluminum and Al-O integrated circuit depositions is less than $10^{-5}$ Torr. The mean free path between gas-phase collisions at such pressures is greater than 500 cm. Consequently, the aluminum atoms evaporated from the E-beam source crucible execute approximately straight line trajectories to the substrate. Since the sticking coefficient for an aluminum atom on any wall it strikes is essentially unity, there are very few large-angle scattered aluminum atoms in chamber 10, and the path of aluminum atoms striking an element of area on the chamber wall can be approximated by a straight line from that element of area to the source crucible. Areas which are visually shadowed from the source consequently experience very little aluminum flux. In the areas which are not shadowed, the flux varies as the inverse square of the distance from the source and as the cosine of the angle between the surface normal and the line defining the aluminum-atom path. Reduction of the aluminum atom flux can thus be accomplished by a combination of (1) source-to-monitor distance, (2) monitor canting, and/or (3) periodic monitor shuttering. Embodiments illustrating these arrangements are illustrated in FIGS. 3 to 9 to be described.

For S-gun depositions a different situation exists because of the $2.5 \times 10^{-3}$ Torr argon fill pressure. The mean free path between aluminum-atom/argon-atom collisions is approximately 2.5 cm, and the aluminum atoms experience many collisions in traversing the approximately 30 cm distance between the aluminum source 12 and the integrated-circuit substrates 13. Consequently, aluminum-atom flow is governed by viscous flow relationships for positions within the chamber 10 greater than a few mean free paths away from the aluminum source 12, i.e, for distances greater than about 10 cm. It can be shown that viscous flow ($q_{af}$) of an aluminum atom may be represented by the relationship $$q_{af} = D_a \frac{dn_a}{dr} \qquad (2)$$

where $q_{af}$ is the forward flow of aluminum atoms per square centimeter per second away from a point source assumed at the center of a sphere defined by the walls of the planetary substrate support; $D_a$ is the aluminum diffusion coefficient; $n_a$ is the aluminum atom density and r is the distance from the source. In an S-gun chamber in a $2.5 \times 10^{-3}$ Torr argon environment $D_a$ is approximately $1.6 \times 10^5$ cm$^2$/s. The backward flow of aluminum atoms, $q_{ab}$, i.e. the flow of aluminum atoms back toward the center may be represented by $$q_{ab}/q_{af} = \left( \frac{V_a - V_d}{V_a + V_d} \right) \frac{1 - erf(V_d/V_a)}{1 + erf(V_d/V_a)} \qquad (3)$$

where $V_a$ is the thermal velocity and $V_d$ is the drift velocity of aluminum atoms.

Figure 6:
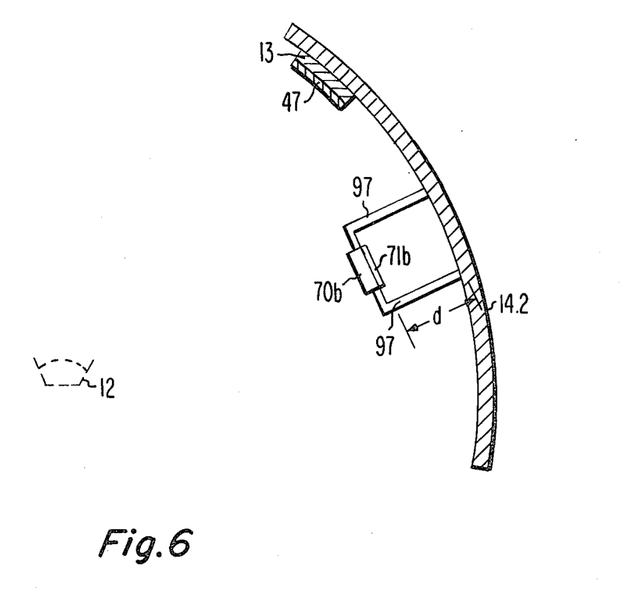
FIG. 6 is a schematic in fragmentary form of another modification of the apparatus shown in FIG. 1 embodied to monitor a sputtering deposition process.
Figure 10:
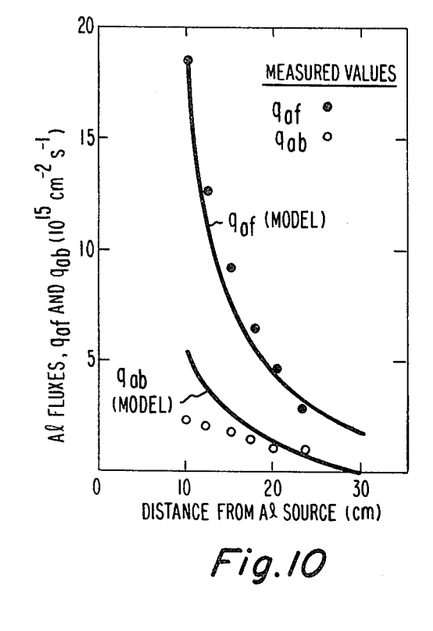
FIG. 10 is a set of curve plots comparing a model to actual tested values of aluminum flux (ordinate) to the distance from the aluminum source (abscissa)

Equations (2) and (3) represent a good model of the aluminum flow in an S-gun deposition chamber. A plot of these equations is shown in FIG. 10 which also contains actual measured values of both the forward and backward flow of aluminum atoms. Both the model and experiment represent a deposition rate of 3.3 angstroms per second. The comparison of the calculated model to the experiment is good for distances greater than 15 cm. The discrepancies in $q_{ab}$ at smaller distances are presumed to suggest "streaming" flow predominates over diffision-limited flow at such distances. FIG. 10 demonstrates the difficulty in reducing the aluminum flux impinging on a monitor surface, the backward flux being a significant fraction of the forward flux throughout the chamber volume. For example, the backward flux at the substrate at r=23.3 cm was $7.4 \times 10^{14}$ cm$^{-2}$s$^{-1}$, a factor of only 2.7 below that experienced by the integrated-circuit substrates. Such a flux reduction factor would not provide a significant increase in resistance-monitor sensitivity required for the present invention. According to the model and experimental data as shown in FIG. 10, only backward-facing locations within approximately 3 cm of the planetary wall will provide reductions greater than a factor of five relative to the integrated-circuit substrate. The embodiment of FIG. 6 illustrates this arrangement, as will be described further.

Figure 11:
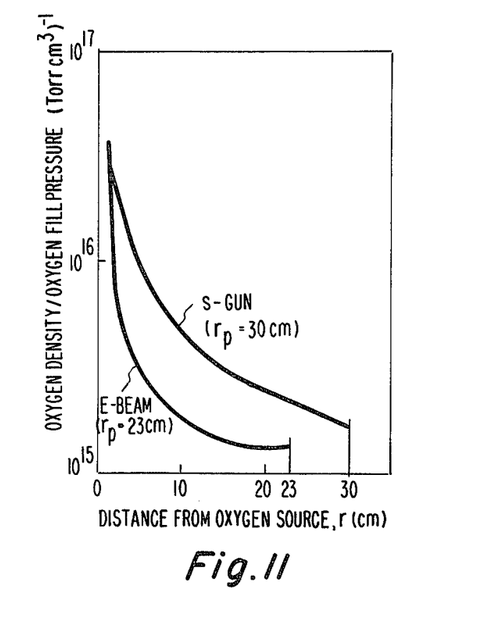
FIG. 11 is a set of curves showing the respective distances from the aluminum source of an E-beam and an S-gun system and the corresponding ratio of oxygen density to fill pressure.

The oxygen density distribution for E-beam and S-gun deposition systems have been calculated for situations in which oxygen is added to the system. FIG. 11 is a plot of such relationships as a function of the ratio of oxygen density to fill pressure ($\eta_o/P_o$) (Torr cm$^3$)$^{-1}$ (ordinate) and distance of the oxygen source in cm from the substrate (abscissa).

It is seen from the curves of FIG. 11 that the density profile levels off asymtotically at a shorter distance from the oxygen source in the E-beam system than in the S-gun system. Accordingly, it appears that it is easier to get a large oxygen-flux multiplication factor in the S-gun system. This phenomenon is utilized in this invention as embodied in FIGS. 7 and 8, to be described.

The principles of the invention will be better understood by reference to several embodiments of the invention illustrated in FIGS. 3–9 now to be described in detail.

Figure 3:
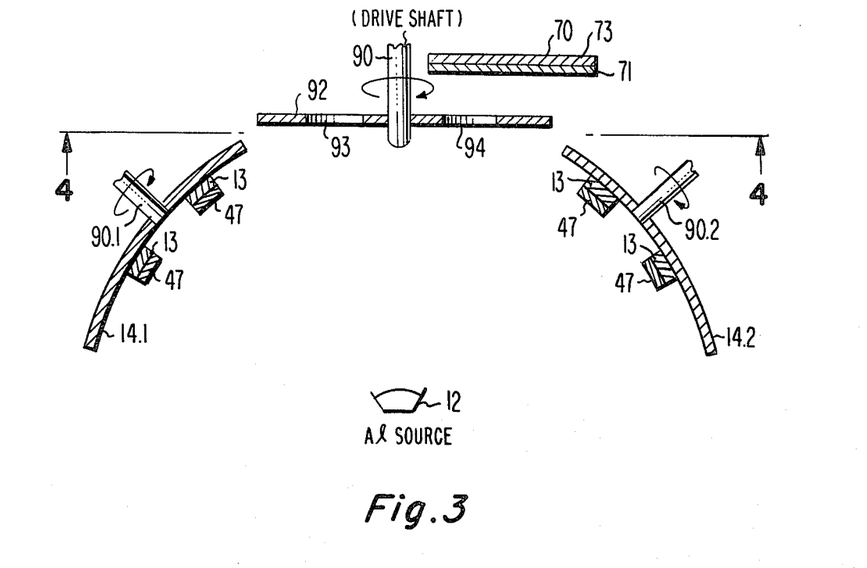
FIG. 3 is a schematic of a modification of the apparatus shown in FIG. 1 embodied as an E-beam evaporator using a shuttered monitor substrate.

FIG. 3 is an illustration of an E-beam deposition system having a monitored substrate that is periodically exposed to the aluminum source through slits or apertures in a shutter 92. The substrates 13 upon which films 47 of aluminum are to be deposited are supported on a pair of planetary supports 14.1 and 14.2, respectively, each rotated about its respective shafts 90.1 and 90.2.

Figure 4:
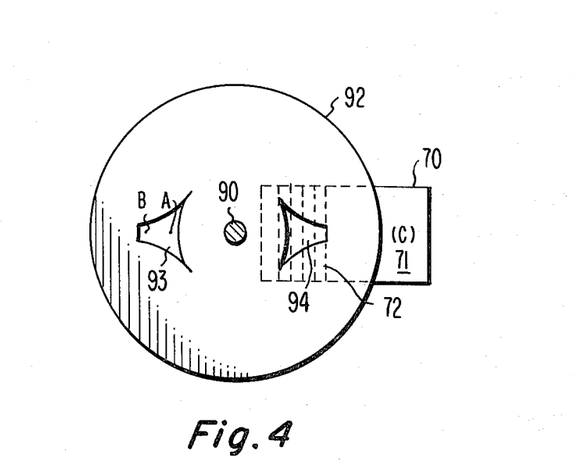
FIG. 4 is a schematic of a section of the apparatus seen along viewing line 4—4 of FIG. 3.

The entire planetary structure is further revolved by a planetary drive shaft 90. The monitor substrate 70 is suitably supported about an opening between the planetery structures in line with the source 12 of aluminum. The shutter 92 in disc form is mounted for rotation on shaft 90. As seen better in FIG. 4, shutter 92 is provided with a pair of triangular apertures 93 and 94. Each aperture provides a window between the aluminum source 12 and the monitor substrate 70 as shown in FIG. 4. Accordingly, an aperture exposes the substrate 70 to the aluminum twice per revolution of the shutter 92. The planetary drive shaft 90 rotates at a speed of approximately one revolution per second. In the laboratory embodiment of the shuttered monitor, the shape of the apertures 93 and 94 which are approximately triangular, provides a shuttering ratio which varies with distance from the axis of shutter 92. This shuttering ratio is approximately four at position A and approximately 30 at position B within the aperture as shown in FIG. 4.

In testing the apparatus, a metal monitor film 72 was deposited on surface 73. Film 72 was then photolithographically patterned into 0.15 cm-wide strips oriented as indicated in FIG. 4 by the dashed lines. Thickness and sheet resistance were measured on each strip individually. In this manner, readings at several different aluminum-flux reduction ratios were obtained from a single monitored substrate 70. A portion of the substrate 70 indicated by C in FIG. 4, was arranged to extend beyond the outer edge of the shutter 92 providing thereby a reference or base line of an unshuttered deposition. The aluminum source-to-monitor distance, that is source 12 to substrate 70, was approximately the same as the source 12 to the planetary 14.1 or 14.2 distance. Accordingly, the test results indicated a substantially equivalent deposition of aluminum on portion C of the substrate 70 as would occur on a substrate 13 mounted on the planetary support 14.1 or 14.2. The results on the shuttered portions of the film, e.g. positions A and B (FIG. 4) and intermediate positions indicated that an oxygen-to-aluminum ratio useful in determining the film resistivity according to the curve 82 of FIG. 2 described above was about 7 to 30.

Figure 12:
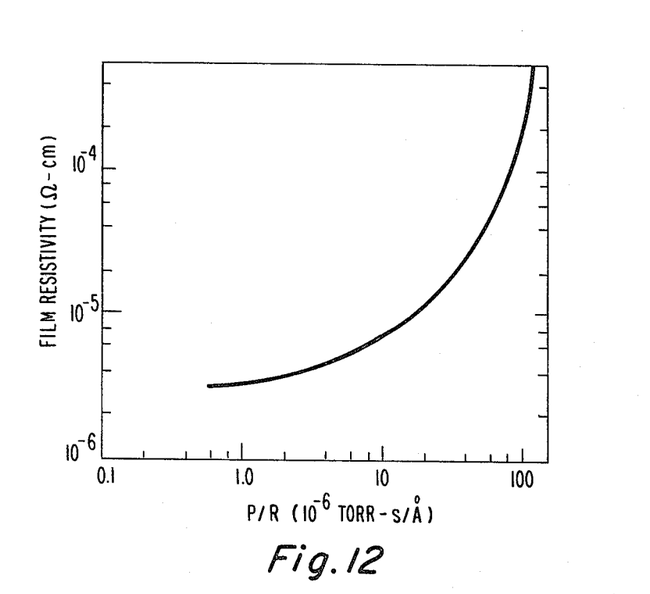
FIG. 12 is a curve of experimental results for shuttered monitors of the type illustrated in FIGS. 3 and 4.

FIG. 12 illustrates a composite resistivity versus pressure to deposition rate ratio curve obtained by a laboratory experiment using monitors that were shuttered. Several monitors were generated in accordance with the photolithographic technique discussed in relation to FIG. 4, buy three deposition runs that were used to generate the curve shown in FIG. 12. Similar curves were generated for the other monitors shown in FIGS. 5, 6, 7 and 8 with results similar to that illustrated by FIG. 12.

In practice, a shuttered monitor according to the embodiment illustrated in FIGS. 3 and 4 will provide for a monitor substrate 70 positioned substantially as shown in FIG. 3 adjacent a shutter 92 in which the apertures 93 and 94 will be shaped to be substantially congruent with the shape of the monitor. In practice, the monitor substrate 70 will typically have the same shape and orientation as one of the individual strips shown in FIG. 3. Accordingly, the apertures 93 and 94 would be triangles bounded by edges which, when extended, would pass through the shutter axis. Such apertures would provide a constant shuttering ratio across the width of the strip.

In operation, electrical contacts to the ends of the substrate 70 and electrical leads to a suitable resistance measuring device may be provided to determine the resistance of the deposited film 71 while the E-beam depositing process is being carried out. Alternatively, if desired, the monitor substrate 70 with deposited film 71 may be removed from the chamber 10 at the end of a deposition for measuring the sheet resistance and the thickness by measurement devices. The sheet resistance measurement together with the thickness is then used to monitor the oxygen content of the film 47 on the substrates 13 used to form the integrated circuit.

Figure 5:
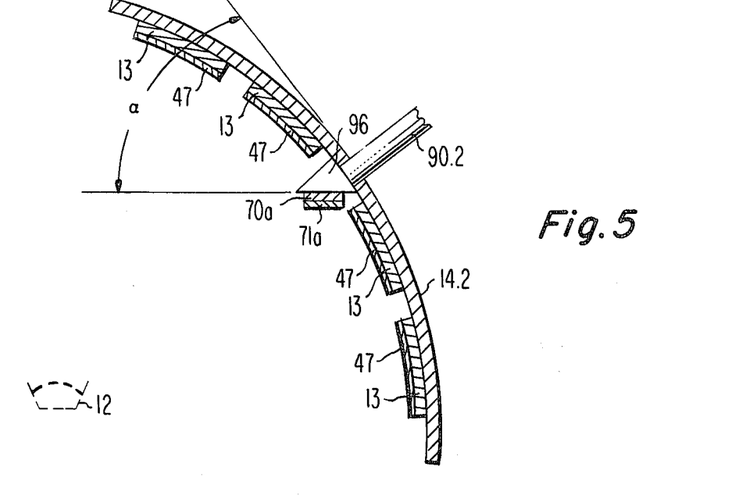
FIG. 5 is a schematic in fragmentary form of another modification of the apparatus shown in FIG. 1 embodied as an E-beam evaporator using a canted monitor substrate.

Reference is now made to FIG. 5 which illustrates in fragmentary form of the apparatus shown in FIG. 1 for an embodiment of the invention in an E-beam deposition chamber using a monitor substrate such as substrate 70a mounted on a bracket 96 attached to one of the planetaries 14.2 (FIG. 3). The bracket is positioned along the axis of shaft 90.2.

In operation, the aluminum flux provides a film 47 of aluminum on the integrated substrates 13 and simultaneously provides a monitor film 71a on the monitor substrate 70a. Because the substrate 70a is canted by an angle $\alpha$ with respect to the adjacent substrates 13, less aluminum will be deposited as the film 71a on the substrate 70a than as film 47 on substrate 13. Accordingly, there will be an increase of the oxygen-to-aluminum ratio in the film 71a. This increase in oxygen-to-aluminum ratio, which increases as the cant angle, $\alpha$, increases, will then provide the desired increase in sensitivity of the film resistivity on the monitor in accordance with the sensitivity curve of FIG. 2 as described hereinabove.

Reference is now made to FIG. 6 illustrating a back-facing monitor of the invention useful in a magnetron sputtering deposition system such as a Varian Model 3120 S-Gun system. A substrate 70b is supported on the planetary 14.2 by bracket 97 at a predetermined distance d. Aluminum from source 12 will be deposited on the rear face of the substrate 70b as a film 71b. The aluminum arrives at the rear face by gas-phase scattering collisions. The mean-free path between such collisions increases with decreasing pressure in the chamber 10. Therefore, the aluminum atom flux to a given position on the surface of monitor substrate 70b decreases with decreasing pressure.

The distance d defining the spacing of the substrate from the planetary 14.2 determines the flux-ratio multiplication factor that can be provided by this arrangement. As the distance, d, is decreased, the aluminum flux to the rear face of substrate 70 will decrease, thereby increasing the flux-ratio multiplication factor. For a sputterer in which the argon fill pressure is $2.5 \times 10^{-3}$ Torr, the dimension d should be less than approximately 3 cm, depending on the multiplication factor desired. At the end of a deposition of aluminum on IC substrates 13 providing an aluminum film layer 47, the film 71b on monitor substrate 70b is measured for sheet resistance and thickness. From these measurements the oxygen-to-aluminum ratio is monitored for the IC substrates 13 in a similar manner as described hereinabove.

Figure 7:
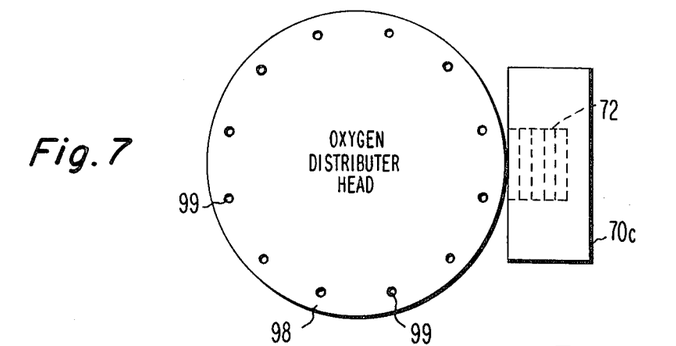
FIG. 7 is a top view schematic of a still further modification of a fragmentary portion of the apparatus shown in FIG. 1 embodied to monitor, in either an E-beam or sputtered aluminum deposition process, the oxygen content in a monitor substrate by which oxygen is periodically or continuously added to the vacuum deposition chamber.
Figure 8:
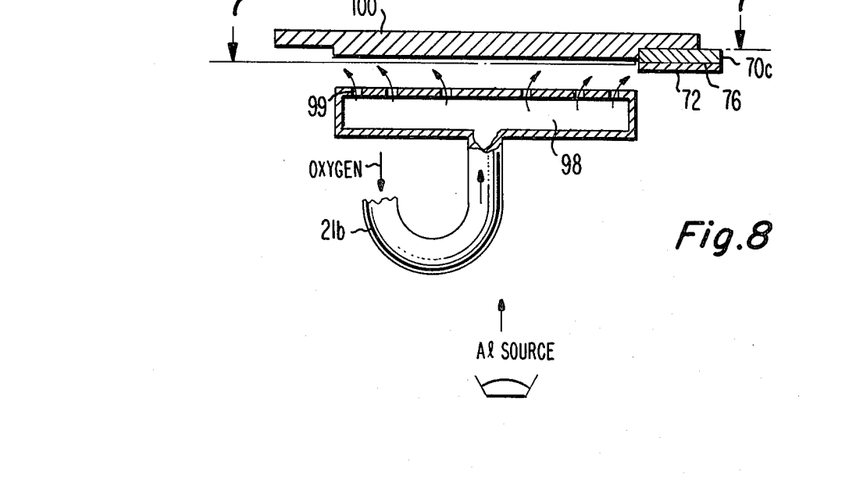
FIG. 8 is a front view of the apparatus shown in FIG. 7.

Reference is now made to FIGS. 7 and 8 which illustrate a monitor substrate useful in practicing the invention in which oxygen is deliberately added to the chamber 10. This form of the invention can be used with either an E-beam deposition system or a magnetron sputterer system.

The monitor substrates hereinabove described in the embodiments illustrated in FIGS. 3–6 have provided means for increasing the oxygen-to-aluminum concentration ratio by decreasing the amount of aluminum flux that is deposited on the monitor substrate relative to that deposited on the IC substrate. Such monitor substrates can be used both for aluminum depositions in a residual gas (water vapor) environment as well as in deposition systems in which oxygen is added. The embodiment illustrated in FIGS. 7 and 8 provides a means to increase the oxygen-to-aluminum flux ratio when oxygen is added during the process of aluminum deposition. The flux ratio is increased by positioning the substrate monitored close to a concentrated source of oxygen thereby increasing the oxygen flux to the monitor relative to the oxygen flux experienced by the IC substrate 13.

In one form of this embodiment arranged to provide experimental data, a monitor 70c is positioned within the chamber close to the source of oxygen. The oxygen via pipe 21b (see FIG. 1) is connected to a distributor head 98 of cylindrical form having a plurality of distributor holes 99. The holes 99, typically 12 in number, are positioned every 30 degrees on a 5 cm diameter circle through which the oxygen exits as indicated by the arrows shown in FIG. 8. The oxygen impinges on a circular diverter plate 100. The substrate 70c is mounted at one portion of plate 100 as shown in FIGS. 7 (plan view) and 8 (front view).

In operation, while the aluminum is being developed in a flux for depositing on the substrate 13 (FIG. 1), the oxygen impinges on the diverter plate 100, forcing thereby a radial flow of oxygen outwardly and in part flowing over the surface of the monitor substrate 76. The source 12 to monitor substrate 70 distance is arranged to be approximately equal to the distance from the source 12 to the planetaries 14.1 and 14.2. Consequently, the monitor substrates 70c experienced approximately the same aluminum-atom flux as that experienced by the IC substrates 13. Since the oxygen flows radially outward across the diverter plate 100 and monitor surface 76, the oxygen flux decreases with increasing distance from the holes 99. Thus, by photolithographically generating a strip pattern in the monitor film 72 after deposition, similar to that used in the embodiment of FIG. 4 described hereinabove, monitor film strips with several different oxygen-to-aluminum ratios can be obtained from a single deposition run. The substrate monitor 70c, with the film 72 deposited thereon, was analyzed as previously described to determine the film thickness and resistivity. These data provided a means to monitor the oxygen-to-aluminum flux ratio in the substrates 13.

For operation in factory production systems, a single monitor strip (calibrated by the multi-strip monitor films shown and described for FIGS. 7 and 8 above), with a fixed oxygen-to-aluminum flux ratio, would be used. This embodiment is applicable to both evaporative (e.g., E-beam) and sputtering (e.g., S-gun) depositions. The shape and configuration of holes 99 are not critical. However, the position of the monitor substrate 70 is critical to the system's operation. It must be close to the oxygen gas source so that it receives on the order of 10 times the oxygen flux that is received by the IC substrates 13 on the planetaries 14.1 and 14.2. The position of the substrate monitor is properly made to implement the film resistivity versus the oxygen pressure to deposition rate ratio curve as illustrated in FIG. 2 described hereinabove to enhance the sensitivity of the oxygen-to-aluminum ratio principle of the invention.

Figure 9:
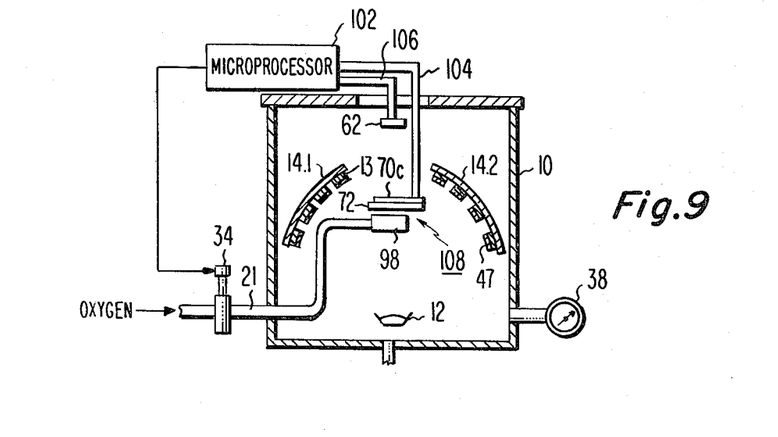
FIG. 9 is a schematic of a monitor with feedback control in a vacuum deposition process for regulating the flow of the reactive gas.

By providing electrical contacts and leads to the monitor substrate 70c, the resistance of the monitor substrate film 72 can be measured continuously during the deposition of aluminum film. Such an arrangement is illustrated in FIG. 9. The vacuum chamber 10 includes the elements described above in connection with FIG. 1 including the aluminum source 12, vacuum gauge 38, the quartz-crystal film-thickness monitor 62, the planetaries 14.1 and 14.2 (FIG. 3) carrying the IC substrates 13. The distributor head 98 is coupled to oxygen via conduit 21 under control of metering valve 34. Metering valve 34 is controlled by a microprocessor 102 adapted to respond both to a signal representing resistance carried on path 104 and to a signal representing thickness carried on path 106. Care must be exercised in positioning the oxygen-source/monitor assembly 108, comprising the oxygen distributor head 98, and the substrate 70c, such that it does not interrupt the aluminum flux to the film thickness monitor 62.

In operation, during the deposition process the monitor substrate 70c provides a resistance signal which, when combined with the thickness measurement from monitor 62, provides a control parameter signal to regulate the flow of oxygen via metering valve 34 so that the ratio of oxygen-to-aluminum in the monitor substrate film 72 is a predetermined value. This predetermined value is selected to provide the desired oxygen-to-aluminum ratio in the substrate 13 film 47.

Although it is not essential in the practice of the invention to establish an absolute calibration between monitor resistivity and IC film oxygen content, such relation if desired can be established by performing a single test deposition containing several monitor substrates with varying multiplication factors and an IC substrate. At the end of the deposition the monitor resistivity versus multiplication factor is determined and the oxygen-concentration versus depth profile on the IC film is performed, for example, as by Auger Electron Spectroscopy.

The various forms the invention that may be embodied as described above are now summarized:

The embodiment of a monitor substrate that is shuttered as illustrated by FIGS. 3 and 4 decreases the aluminum flux to provide thereby the flux ratio multiplication. This monitor is useful in both evaporative and sputtering deposition systems to monitor deposited (1) films of aluminum, (2) films of oxygen doped aluminum, and (3) laminated layers of alternating aluminum and oxygen-doped aluminum layers. Moreover, it can be used to monitor film deposition on an in situ basis whereby the resistance of the monitor substrate may be measured directly on a real time basis.

The embodiment illustrated in FIG. 5 provides for a canted monitor substrate which also functions to decrease the aluminum flux to provide thereby the flux ratio multiplication. It is useful primarily in evaporative (E-beam) deposition systems. Moreover, it is useful primarily for aluminum films and oxygen-doped aluminum films. It does not lend itself particularly to an in situ real time resistance measurements. In practice, the canted monitor substrate is removed from the chamber after the deposition to determine the resistance or resistivity of the film of the monitor substrate film.

The monitor substrate that is facing away from the aluminum flux source, namely, the back-facing monitor substrate, as illustrated in FIG. 6, also provides for decreased aluminum flux to provide the flux ratio multiplication. However, it is useful only in sputtering deposition systems in which aluminum films or oxygen-doped aluminum films are deposited. Furthermore, it does not lend itself to in situ, real time resistance measurement techniques.

The monitor that depends upon enhanced oxygen to the monitor substrate during the deposition process of the aluminum film is illustrated by FIGS. 7 and 8. In this embodiment, it is the increased flux of oxygen that is used to provide the flux ratio multiplication. This form of the invention is useful for both evaporative as well as sputtering deposition systems. It is useful for film depositions of oxygen-doped aluminum as well as laminated films comprising alternating layers of aluminum and oxygen-doped aluminum. This embodiment is useful for in situ film resistance measurement as as illustrated, for example, by the embodiment of FIG. 9.

It will now be appreciated in view of the above description of the several embodiments of the invention that a monitor substrate is provided to monitor the oxygen concentration in the aluminum of integrated circuit metallizations by detecting changes in the monitor film resistivity or merely the resistance in a calibrated system.

What is claimed is:

1. A method of monitoring the concentration of oxygen in an aluminum-based film deposited in a vacuum chamber in which there is residual gaseous oxygen-specie comprising the steps of:
   providing a flux of aluminum in the chamber;
   depositing aluminum simultaneously both on a monitor substrate and at least one IC substrate such that the ratio of oxygen concentration to aluminum concentration on said monitor substrate is significantly greater than said ratio on said IC substrate; and
   measuring the resistivity of the deposited aluminum film on said monitor substrate, the resistivity value on said monitor substrate having a much higher sensitivity to the oxygen content in said monitor film as compared to the sensitivity of the resistivity of the IC film to its oxygen content.

2. The method according the claim 1 wherein the step of measuring the resistivity includes the step of measuring the resistance of the deposited aluminum film on the monitor substrate and calibrating the resistance value to determine the resistivity of said film on the monitor substrate.

3. The method of claim 1 further comprising the step of periodically interrupting the flux of aluminum passing to the monitor substrate by a moving shutter having an aperture to pass the flux periodically.

4. The method of claim 1 for use in an evaporation-type deposition chamber further comprising the step of positioning the monitor substrate within the chamber closely adjacent said one IC substrate at an angle that is canted with said IC substrate such that the amount of aluminum deposited on said monitor substrate is less than the aluminum deposited on said IC substrate.

5. The method of claim 1 for use in a magnetron sputter-type deposition chamber further comprising the step of positioning the monitor substrate closely adjacent said one IC substrate and orienting the surface upon which aluminum film is deposited in an opposite direction to the deposited film on said IC substrate.

6. The method according to claim 1 further comprising the step of introducing oxygen into the chamber to dope the aluminum being deposited on said IC substrate with oxygen; and
   controlling a portion of said flow of oxygen towards said monitor substrate such that the oxygen disposed on said monitor substrate is significantly greater than the oxygen disposed on said IC substrate.

7. The method according to claim 3 or 6 further comprising the steps of interrupting the flow of oxygen periodically to develop a lamination of alternating layers of aluminum and oxygen doped aluminum both on said IC substrate and on said monitor substrate.

8. In a vacuum chamber for depositing aluminum on an integrated circuit (IC) substrate, said chamber including means to provide a flux of said aluminum to deposit aluminum on said IC substrate, said chamber having a residual gaseous oxygen-specie during the aluminum deposition, the improvement comprising:
   monitoring means for monitoring the ratio of oxygen to aluminum on said IC substrate, said means including means for depositing the film of aluminum on a monitor substrate concurrently with the deposition of aluminum film on said IC substrate such that the resistivity of said monitor substrate film is significantly greater than the resistivity of aluminum film deposited on said IC substrate.

9. In a vacuum chamber according to claim 8 further including means for measuring the resistivity of said monitor substrate film.

10. In a vacuum chamber according to claim 8 further including means for measuring the resistance of said monitor substrate film.

11. In a vacuum chamber according to claim 8 wherein said monitoring means includes a monitor substrate positioned in said chamber to be exposed periodically to said flux of aluminum, said means including a shutter having an aperture and moved to pass the flux of aluminum through the aperture onto said monitor substrate periodically.

12. The vacuum chamber according to claim 8 wherein said chamber is arranged to provide aluminum by evaporative deposition and further wherein said monitoring means includes a monitoring substrate positioned in said chamber closely adjacent said IC substrate and canted with respect to said IC substrate such that the aluminum deposited on said monitor substrate is significantly less than the aluminum deposited on said IC substrate.

13. The vacuum chamber according to claim 8 wherein said chamber is arranged to provide aluminum by magnetron sputtering deposition in an argon gas environment and further wherein said monitoring means includes a monitor substrate positioned in said chamber to face away from the aluminum source such that aluminum deposited on said monitor substrate occurs primarily by collisions of the aluminum atoms of the flux with argon atoms.

14. The vacuum chamber according to claim 8 further including means for providing a flow of oxygen into said chamber to dope the deposited film of aluminum on said IC substrate with oxygen and further means for controlling a portion of the flowing oxygen to be directed to the monitor substrate so that the concentration of oxygen in the aluminum film deposited on the monitor substrate is significantly greater than the concentration of oxygen in the IC substrate film.

15. The vacuum chamber according to claim 14 further including means for automatically controlling flow of oxygen by feedback means responsive to a signal representing the resistivity of said substrate monitor.

* * * * *